United States Patent [19]

Chen et al.

[11] Patent Number: 5,780,073
[45] Date of Patent: Jul. 14, 1998

[54] APPARATUS OF SHAPING A CATHETER TIP

[75] Inventors: Jui-Hsiang Chen; Shu-Fang Jiang; Ken-Yuan Chang, all of Hsinchu; Ruey-Wen Hwang, Tao Yuan; Huei-Ming Ding, Chupei, all of Taiwan

[73] Assignee: Industrial Technology Research Institute, Hsinchu, Taiwan

[21] Appl. No.: 832,627

[22] Filed: Apr. 4, 1997

[30] Foreign Application Priority Data

Feb. 11, 1997 [TW] Taiwan .................. 86101495

[51] Int. Cl.⁶ .................................................. B29C 55/22
[52] U.S. Cl. ..................... 425/289; 219/243; 264/291; 425/384; 425/392
[58] Field of Search ............................. 425/384, 392, 425/393, 289, DIG. 53; 264/291, 327; 219/243

[56] References Cited

U.S. PATENT DOCUMENTS

| | | | |
|---|---|---|---|
| 2,571,416 | 10/1951 | Brown | 264/339 |
| 2,596,933 | 5/1952 | Kirk | 219/243 |
| 3,125,619 | 3/1964 | Miller | 264/327 |
| 3,376,606 | 4/1968 | Deines | 425/384 |
| 3,608,146 | 9/1971 | Dunipace | 425/DIG. 53 |
| 3,982,992 | 9/1976 | Moffit | 219/243 |
| 4,212,204 | 7/1980 | St. Amand | 264/291 |
| 4,404,159 | 9/1983 | McFarlane | 264/296 |
| 4,412,123 | 10/1983 | Ammann et al. | 219/243 |
| 4,834,637 | 5/1989 | Conta et al. | 425/173 |
| 5,209,882 | 5/1993 | Hattori et al. | 264/291 |
| 5,547,364 | 8/1996 | Wong et al. | 425/392 |

FOREIGN PATENT DOCUMENTS

WO92/21508   12/1992   WIPO .................. 264/291

*Primary Examiner*—Robert Davis
*Attorney, Agent, or Firm*—Sughrue, Mion, Zinn, Macpeak & Seas PLLC

[57] ABSTRACT

A method of shaping a catheter tip and an apparatus for shaping a catheter tip are disclosed. A hollow tube is radically preheated, which is non-contact thermoforming. The heated tube is then extent outwards and next cooled. After cut, at least two catheters with taper-shaped tip are formed. The apparatus for shaping the catheter tip includes a twin taper-shaped mold wound by heating coil, a tube extending device, a cooling device and a cutting device.

13 Claims, 6 Drawing Sheets

APPARATUS OF SHAPING A CATHETER TIP

BACKGROUND OF THE INVENTION

1. Field of the Invention

The invention relates in general to the fabrication of a catheter tip, and more particularly to a non-contact thermal shaping method to fabricate the catheter tip.

2. Description of the Related Art

A catheter is a tube applied in medical diagnosis or therapy. Most of the catheters are invasive use in digestion system, urinary system, or circulation system. As the catheter is inserted into a patient's body in the aid of other auxiliary instruments, pain or uncomfortable sensation usually occurs to the patient. To reduce the pain and prevent the patient's organs from injury, it is necessary to shaping the catheter tip to improve the catheter inserting process.

A shaping apparatus and method for forming a surgical catheter tip is proposed in an U.S. Pat. No. 5,102,324 by Bullard. The apparatus is mainly comprised of a mold, a mold heater, a clamping pad, and a cooling device. The process for shaping a catheter tip according to the invention of Bullard is illustrated in FIG. 1, which includes: step 102, preheating the mold to a certain temperature, step 104, placing a catheter in the clamping pad to fix its position, step 106, pushing the catheter in the clamping pad into the preheated mold, step 108, leaving the catheter in the mold until the tip of the catheter is formed, step 110, air-cooling the catheter with desired tip configuration, step 112, removing the catheter from the mold, step 114, releasing the catheter from the clamping pad, and step 116, cutting the catheter, which is now a complete surgical catheter tip 118.

A method and apparatus of manufacturing a plastic tube to have a tapered tip is disclosed in U.S. Pat. No. 4,404,159. A mandrel is firstly inserted into the plastic tube. Then, the mandrel along with the plastic tube is pushed into a heated model with a tape-shaped concave, using a slippery workbench. After being left in the model for a certain period of time, the plastic tube is softened and shaped by the model to have a tapered tip. A plastic tube having a desired tapered tip is then completed after cooled and removed from the model.

A method of improving the removal of the catheter from the model during the formation process of the catheter is disclosed in U.S. Pat. No. 4,904,433. The improved removal step is obtained by coating a concurring aminoalkyl terminated polysiloxane lubricant on the surface of the unprocessed catheter, pushing the lubricant coated catheter along with the inserted mandrel into a heated model for a certain period of time. Therefore, the shape of the catheter tip is changed according to the shape of the inner concave of the model. The lubricant coated on the catheter tip helps the removal of the catheter from the model.

A method of fabricating an elbowed end catheter, U.S. Pat. No. 4,292,270, is disclosed. An end of a thermoplastic hollow tube is inserted into a hollow curve-model with a tube shape. As the model is heated to a temperature higher than the melting point of the tube, the tube is than pushed into the model so that the catheter is shaped to have an elbowed end. After cooling and removal from the model, the elbowed end catheter is than completed.

A catheter with a special tip design is disclosed in U.S. Pat. No. 4,588,398. The catheter according to this invention has a tapered outerwall and a tip with a certain angle. This kind of catheter can be further soaked in lubricant. The soaking step is asserted to reduce rubbing as the catheter is inserted into the patient's body.

An apparatus for sealing an end of a hollow thermoplastic tube is disclosed in U.S. Pat. No. 4,373,894. This apparatus includes a female die, which has a certain inner concave configuration. As the female die is heated to the softening temperature of the plastic tube, the plastic tube is inserted to the inner concave to have a plastic tube with a sealed end.

SUMMARY OF THE INVENTION

It is therefore an object of the invention to provide a non-contact heating process for the tube, which prevents the catheter from contamination. Moreover, since the mold in accordance with the invention does not directly contact with the tube, there is no need to use lubricant to help separating the mold and the tube.

It is another object of the invention to provide a method of shaping a catheter tip and an apparatus for shaping a catheter tip. A hollow tube is radically preheated, which is non-contact thermoforming. The heated tube is then extended outwards and next cooled. After cut, at least two catheters with taper-shaped tip are formed. The apparatus for shaping the catheter tip includes a twin taper-shaped mold wound by heating coil, a tube drawing device, a cooling device and a cutting device.

BRIEF DESCRIPTION OF THE DRAWINGS

Other objects, features, and advantages of the invention will become apparent from the following detailed description of the preferred but non-limiting embodiments. The description is made with reference to the accompanying drawings in which.

DESCRIPTION OF THE PREFERRED EMBODIMENT

Figure 1:
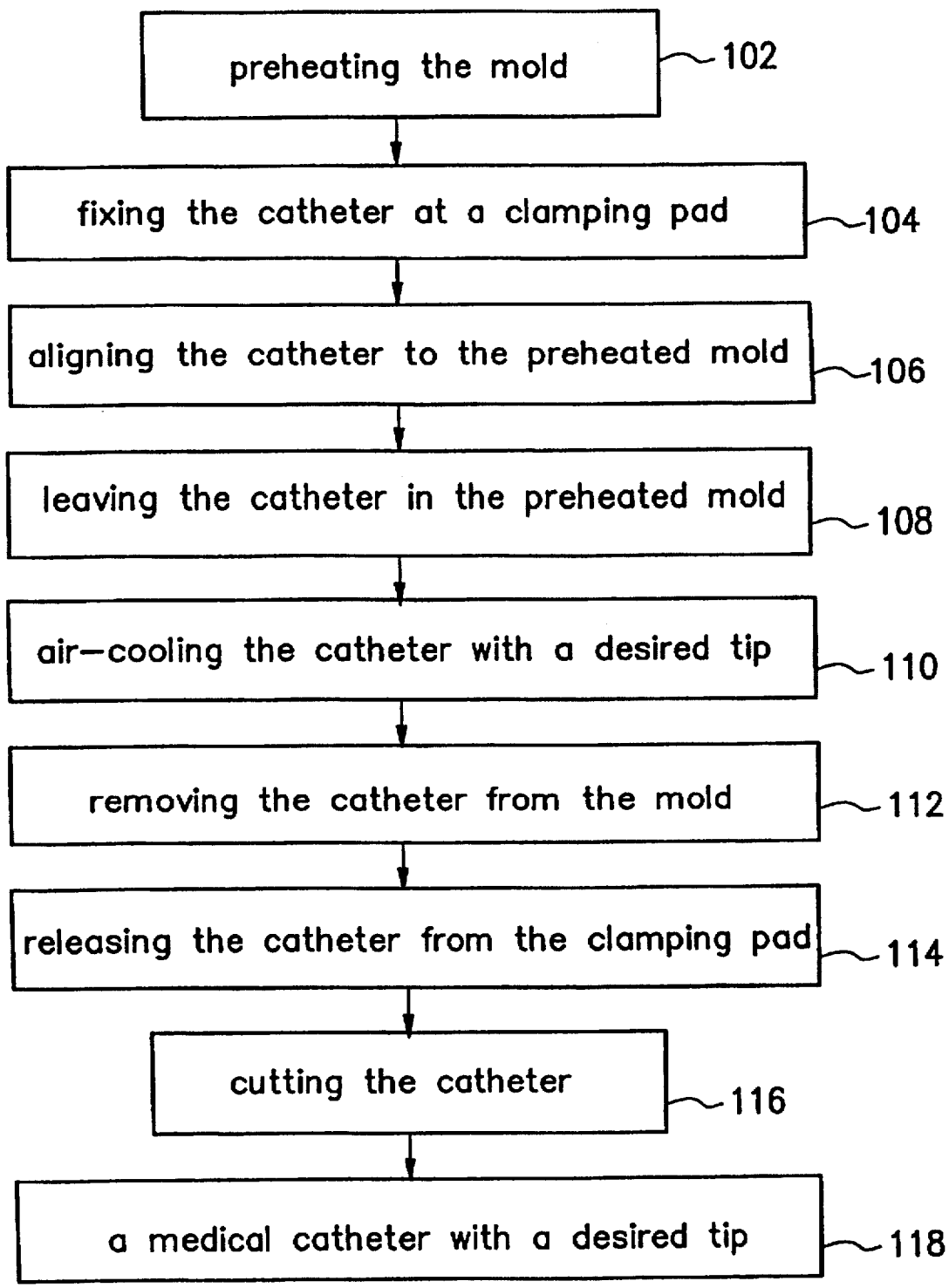
FIG. 1 is a process flow for fabricating a conventional catheter tip.
Figure 2:
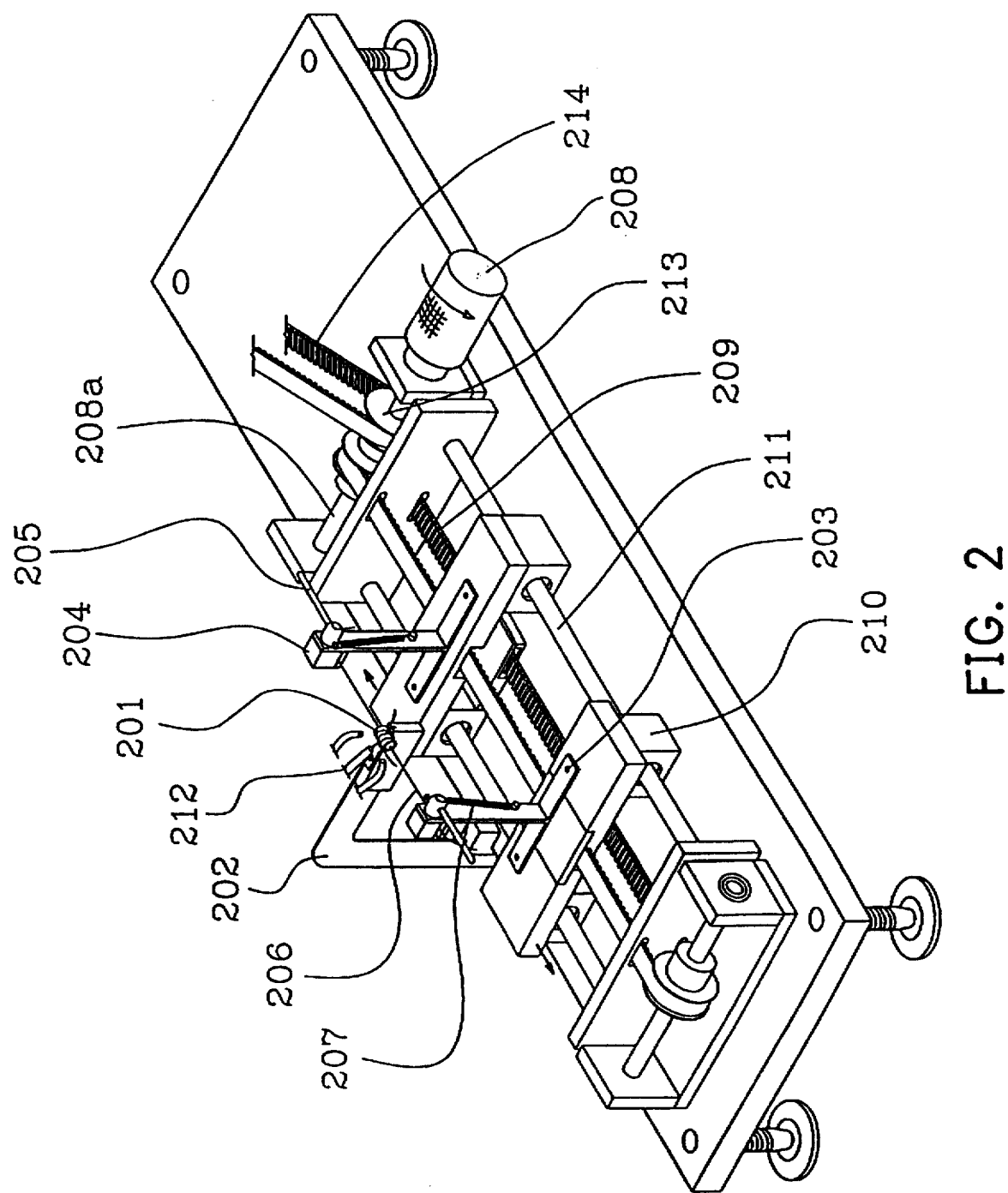
FIG. 2 is an apparatus for shaping a catheter tip in accordance with a preferred embodiment of the invention.

FIG. 2 illustrates an apparatus for shaping a catheter tip. The apparatus includes a heating device 201 with a twin-taper shaped inner concave, a bracket 202 to support the heating device 201, a tube drawing device and a cooling device. The tube drawing device includes a fixture set 204 fixed on a slipping block set 210 by a screw 203, a driving shaft 208a transmits the slipping block set 210 through a driving band 209. The driving shaft 208a can be either connected to a handle 208, which is therefore manually controlled, or to any kind of power supply. The cooling device is preferably a forcible cooling device 212.

Figure 3A:
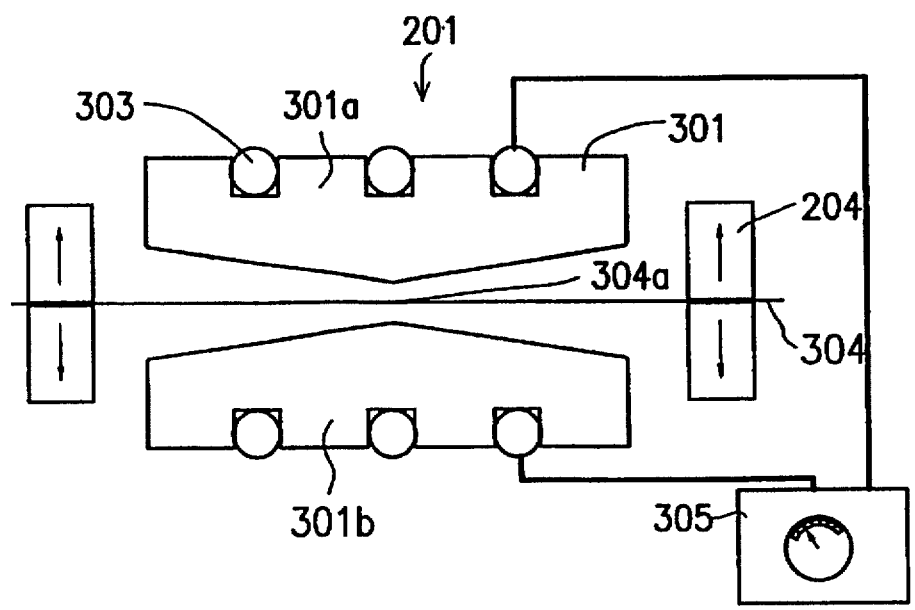
FIGS. 3A to 3F show the process steps of shaping the catheter tip in accordance with a preferred embodiment of the invention.
Figure 3B:
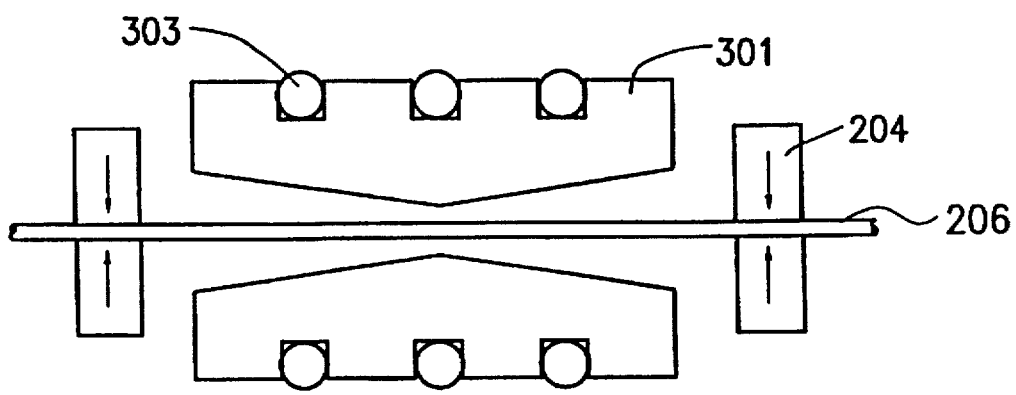

FIG. 3A illustrates the heating device 201. The heating device 201 includes a twin taper-shaped mold 301, a heating coil 303 winding the mold 301, and a temperature controller 305 controlling the heating rate. The temperature controller 305 is not shown in FIGS. 3B to 3F to simplify the drawings. The twin taper-shaped mold 301 includes a first taper-shaped mold 301a and a second taper-shaped mold 301b. The two taper-shaped mold 301a and 301b are mirror image to each other and the apexes of the two taper-shaped mold 301a and 301b are pointed to each other. Line 304 represents a central line between the two taper-shaped mold 301a and 301b. Consequently, the center point 304a between the apexes of the two taper-shaped mold 301a and 301b has the highest heating rate and the heating rate decreases at the points away from the center. This heating status therefore causes a temperature gradient effect on plastic tube.

Referring to FIG. 2, a heating device 201 is first fixed at the bracket 202. By adjusting the height of the bracket 202 and the screw 203, the central line 304 between the two taper-shaped mold 301a and 301b is aligned to the slit of the fixture set 204. Next, the fixture set 204 is opened, using the opening handle. After that, a hollow tube 206 made of, for example, thermoplastic polymer, is placed at the fixture set 204, which is then automatically shut by the spring 207. The twin taper-shaped mold 301 is heated at a desired heating speed until a temperature higher enough to soften the tube. As the tube begins to soften, a driving force is given to the driving shaft 208a, which indirectly transmits the fixture set 204 to move along with a guiding bar 211. The softened tube 206 is extended for a certain length and then left still for a few seconds, for example, 2 to 6 seconds. After the tube is ended with a configuration which is narrowest at the center and becomes wider at the points away from the center, the heating process is stopped and the forcible air-cooling device 212 is operated so that both the tube 206 and the mold 301 are cooled down. After removed from the fixture set 204, the tube is cut by, for example, a knife, to obtain a final product, which can be used as a catheter.

The tube drawing device can be manually controlled. Furthermore, it can be automatically controlled by connecting the driving band 214 on a gear 213 of the tube drawing device to a serve-controller (not shown).

Figure 3C:
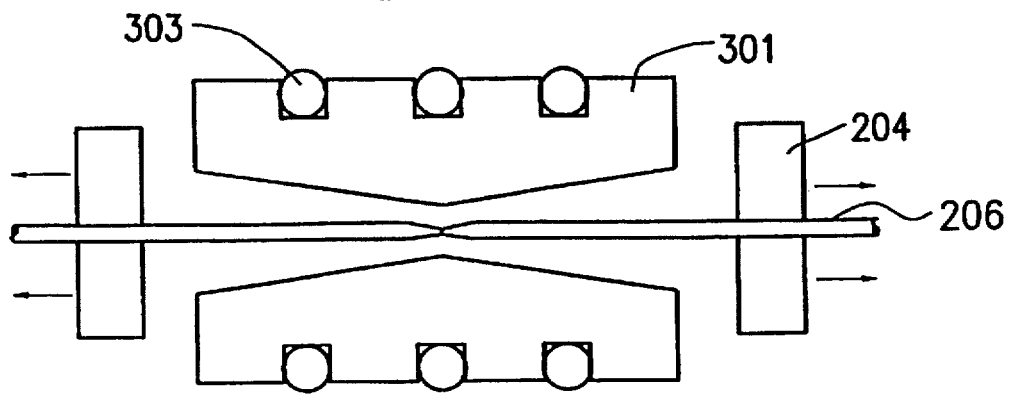
Figure 3D:
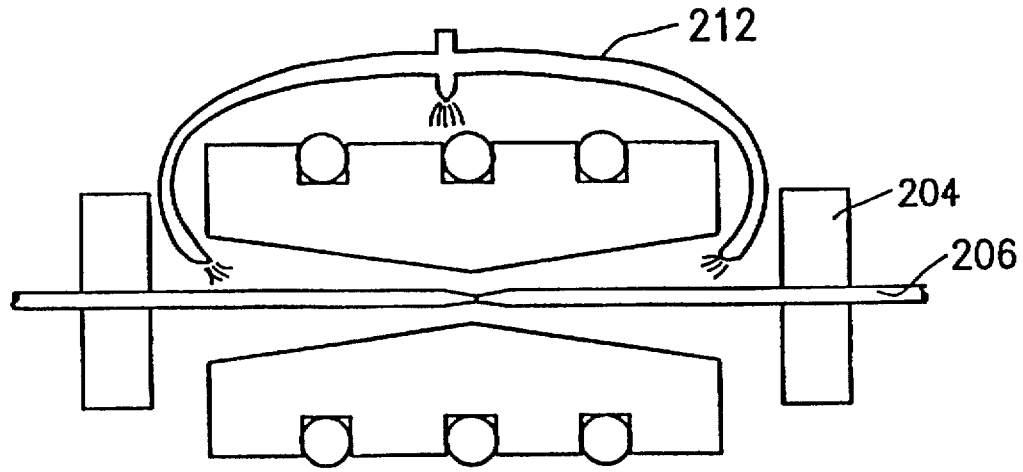
Figure 3E:
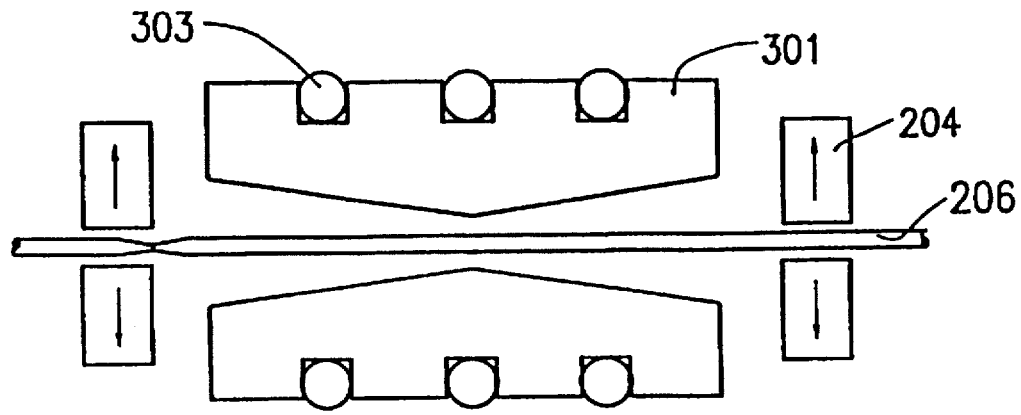
Figure 3F:
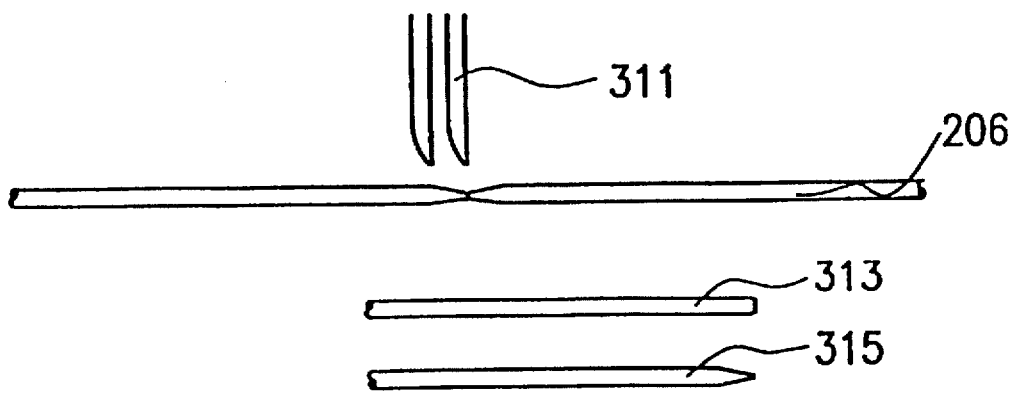
Figure 4:
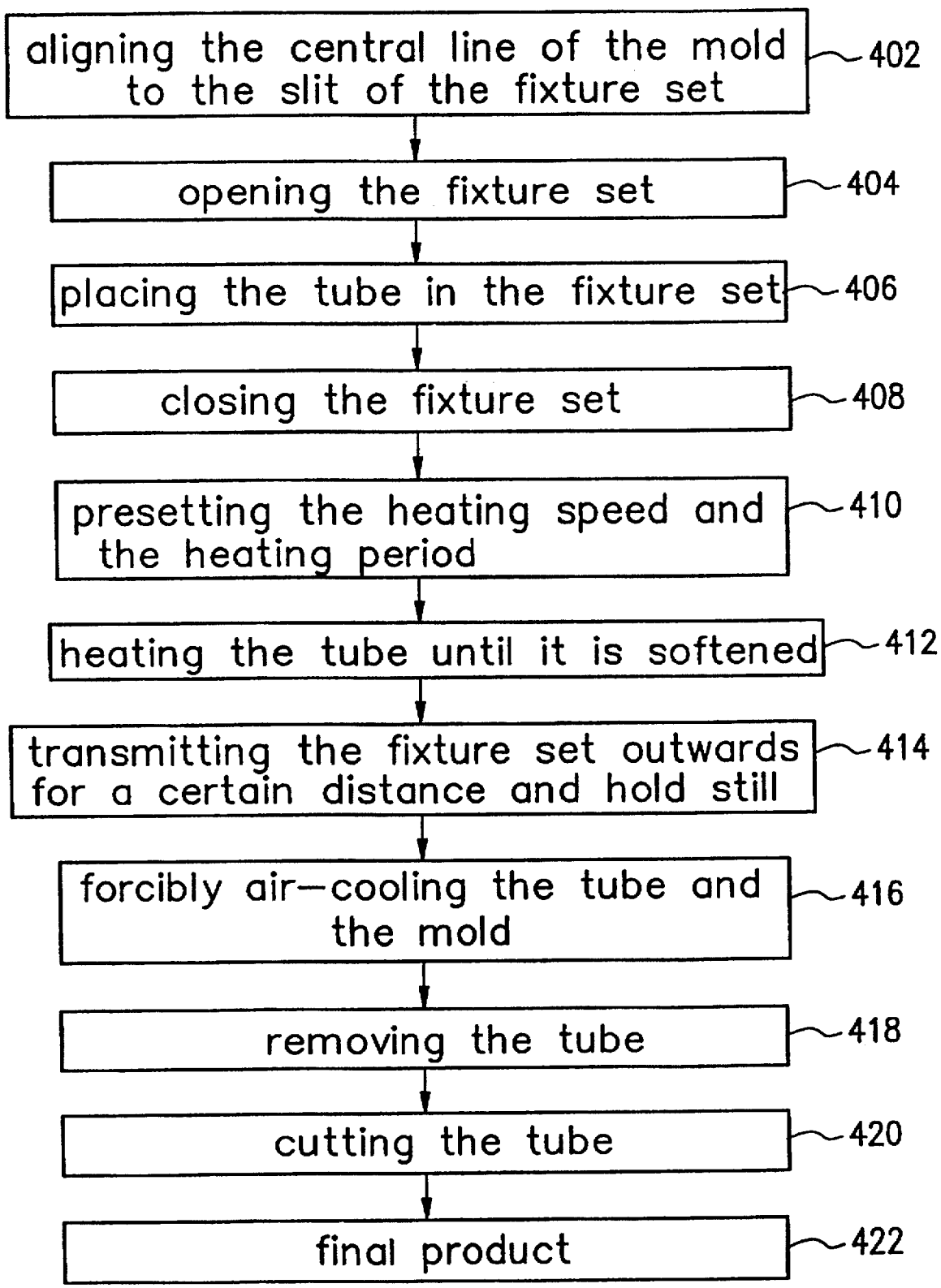
FIG. 4 is a flow chart corresponding to FIG. 3A to FIG. 3F.

FIG. 3A through 3F and FIG. 4 more clearly illustrate the process step and the process flow according to the invention. First, referring to FIG. 3A and the corresponding steps 402 and 404 in FIG. 4, the central line 304 between the two taper-shaped mold 301a and 301b is aligned to the slit of the fixture set 204. Next, the fixture set 204 is opened. Then, referring to FIG. 3B and steps 406 and 408, the tube 206 is placed and fixed at the fixture set 204. Referring to FIG. 3C and steps 410, 412 and 414, the tube 206 in the mold 301 is heated to soften at a certain speed for a certain period; the fixture set 204 is then moved outwards for a certain distance and then kept still. Referring to FIG. 3D and step 416, the tube 206 and the mold 301 are both cooled down by the air-cooling device 212. Referring to FIG. 3E and step 418, the fixture set 204 is released to remove the tube 206. Referring to FIG. 3F and steps 420 and 422, the tube 206 is than cut by the knife 311 to form a final product, for example, a catheter. Catheters with tips of different shapes and sizes, such as tube 313 and tube 315, can be obtained by cutting different points of the catheters.

Figure 5:
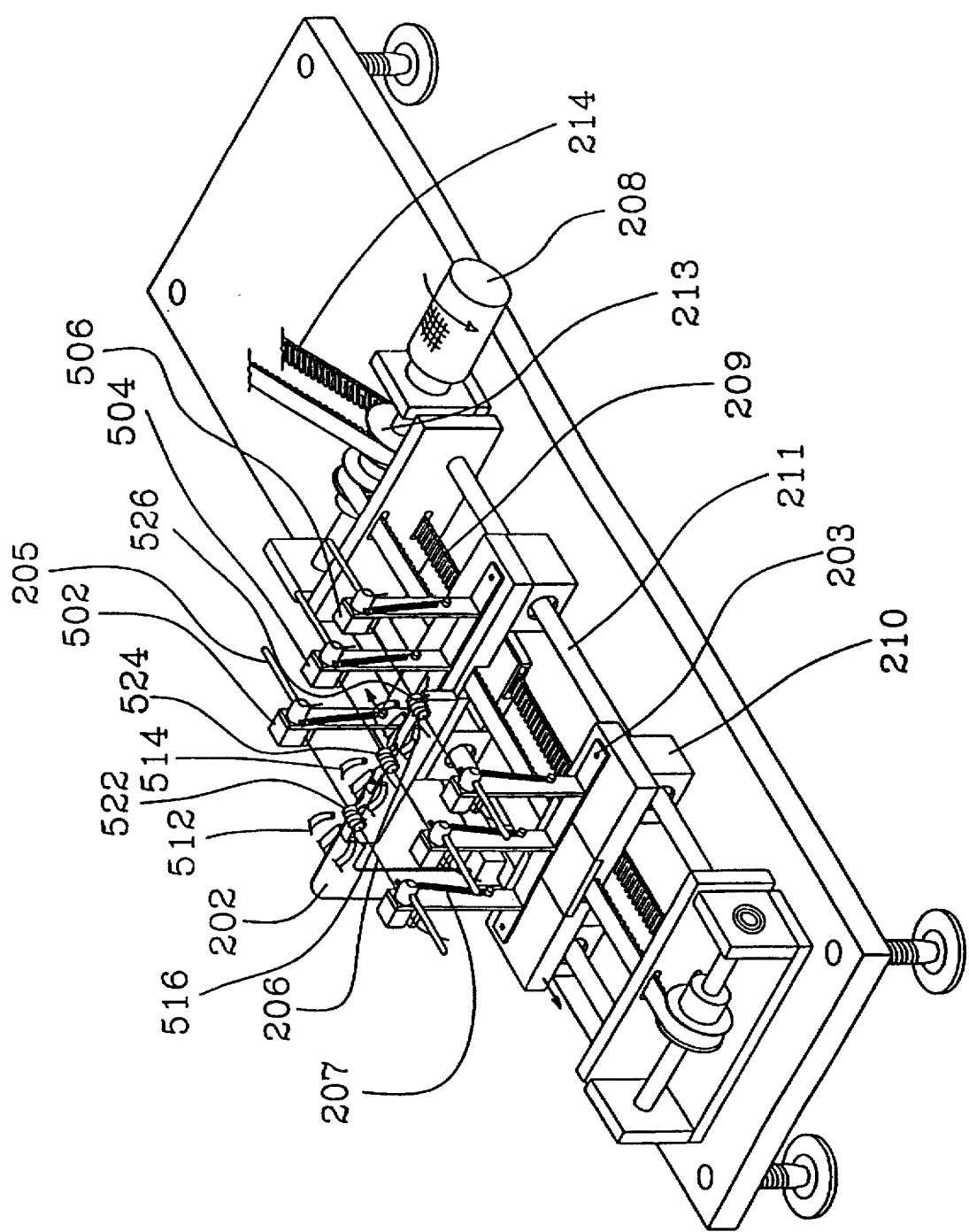
FIG. 5 is an apparatus for shaping a catheter tip in accordance with another preferred embodiment of the invention.

The apparatus for fabricating catheters according to the above-mentioned preferred embodiment is suitable to form a couple of catheters in a process cycle. However, this invention is not limited in this scope. More than a couple of catheters can be formed in a process cycle. For example, an apparatus which can form three couples of catheters in a process cycle is illustrated in FIG. 5. This apparatus includes three sets of fixtures 502, 504, and 506, three cooling devices 512, 514, and 516, and three sets of twin taper-shaped molds 522, 524 and 526. According to this spirit, several couples of catheters can be formed in a process cycle.

To sum up, the apparatus and the method for fabricating a catheter tip according to the invention have the following characteristics.

1. The tube is radically heated without contacting the tube, which prevents the catheter tip from contamination.
2. There is no requirement of additional lubricant since lubricant is only needed as the thermoformation process is a contact process.
3. The twin taper-shaped mold according to the invention contributes a temperature gradient. Controlling the shape of the twin taper-shaped mold can consequently modify the shape of the catheter tip.
4. Controlling the drawing speed and distance can also modify the shape of the catheter tip.
5. Cutting the after-thermoformated tube at different points makes catheters with different tip shapes.
6. A number of tubes can be processed at a time to increase throughput.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. An apparatus for shaping a catheter tip, comprising:
    a twin taper-shaped heating device to heat a hollow tube;
    a tube drawing device to extend the hollow tube;
    a cooling device to cool the hollow tube; and
    a cutting device to cut the hollow tube.

2. An apparatus according to claim 1, wherein changing the angle of the twin taper-shaped heating device results in the configuration change of the tube.

3. An apparatus according to claim 1, wherein the heating device comprises:
    a twin taper-shaped mold, wherein the twin taper-shaped mold includes a first taper-shaped mold and a second taper-shaped mold;
    a heating coil which winds the first taper-shaped mold and the second taper-shaped mold; and
    a temperature controller to adjust the heating speed.

4. An apparatus according to claim 3, wherein the heating device further comprises a bracket to support the heating device.

5. An apparatus according to claim 4, wherein the position of the twin taper-shaped mold is adjusted by the bracket.

6. An apparatus according to claim 3, wherein the twin taper-shaped mold is made of metal.

7. An apparatus according to claim 1, wherein the tube drawing device comprises:
    a fixture set which fixes the hollow tube to alighted to the center of the heating device;
    a slipping block set which transmits the fixture set; and
    a driving shaft which transmits the slipping block set.

8. An apparatus according to claim 7, wherein the tube drawing device comprises more than two fixture sets.

9. An apparatus according to claim 7, wherein the fixture set is fixed at the slipping block.

10. An apparatus according to claim 7, wherein the driving shaft is connected to a manually-controlled handle.

11. An apparatus according to claim 7, wherein the driving shaft is connected to a power supply.

12. An apparatus according to claim 1, wherein the cooling device is a forcible cooling device.

13. An apparatus according to claim 1, wherein the cutting device is a knife.

* * * * *